United States Patent [19]

Nemec et al.

[11] 4,443,383

[45] Apr. 17, 1984

[54] PREPARATION OF METHACROLEIN AND METHACRYLONITRILE FROM TERT-BUTYL ALKANOATES

[75] Inventors: Joseph W. Nemec, Rydal; Michael S. Cholod, Cornwells Heights, both of Pa.

[73] Assignee: Rohm and Haas Company, Philadelphia, Pa.

[21] Appl. No.: 400,491

[22] Filed: Jul. 21, 1982

Related U.S. Application Data

[60] Division of Ser. No. 245,296, Mar. 19, 1981, Pat. No. 4,358,622, which is a continuation-in-part of Ser. No. 84,255, Oct. 12, 1979, abandoned.

[51] Int. Cl.³ .................. C07C 120/00; C07C 121/32
[52] U.S. Cl. ............................. 260/465.2; 260/465.9
[58] Field of Search ........................... 260/465.9, 465.2

[56] References Cited

U.S. PATENT DOCUMENTS

| | | | |
|---|---|---|---|
| 3,026,362 | 3/1962 | McKeever | 560/247 |
| 3,365,482 | 1/1968 | Khoobiar | 260/465.3 |
| 3,907,712 | 9/1975 | Ohara et al. | 252/456 |
| 3,933,686 | 1/1976 | Ferlazzo et al. | 260/465.3 X |
| 3,936,503 | 2/1976 | Miller, Jr. et al. | 260/501.15 X |
| 3,936,505 | 2/1976 | Oda et al. | 252/437 X |
| 4,011,272 | 3/1977 | Matsuzawa et al. | 568/895 |
| 4,035,418 | 7/1977 | Okada et al. | 252/539 X |
| 4,049,575 | 9/1977 | Sasaki et al. | 252/439 |
| 4,065,507 | 12/1977 | Hardman et al. | 568/477 |
| 4,078,004 | 3/1978 | Schlaefer et al. | 260/604 R |
| 4,111,984 | 9/1978 | Ishii et al. | 252/443 X |
| 4,138,430 | 2/1979 | Stiles et al. | 260/465.9 |

FOREIGN PATENT DOCUMENTS 819255  12/1974  Belgium .

OTHER PUBLICATIONS

C.A. 86, (1977), Mitsubishi, 86:4926e.

*Primary Examiner*—Joseph Paul Brust
*Attorney, Agent, or Firm*—Terence P. Strobaugh

[57] ABSTRACT

The present invention relates to a process of the conversion of tert-butyl alkanoates to methacrolein or methacrylonitrile, and more particularly to a process for the conversion of tert-butyl acetate to methacrolein or methacrylonitrile.

1 Claim, No Drawings

PREPARATION OF METHACROLEIN AND METHACRYLONITRILE FROM TERT-BUTYL ALKANOATES

This is division of application Ser. No. 245,296 filed Mar. 19, 1981 now U.S. Pat. No. 4,358,622 which was a continuation-in-part application of U.S. Ser. No. 84,255, filed Oct. 12, 1979, now abandoned.

BACKGROUND OF THE INVENTION

Isobutylene is usually produced in petroleum refineries and in ethylene plants as an ingredient in a mixture of butane and butenes. Isobutylene is usually separated from the other materials by absorption in an inorganic acid such as sulfuric acid. It is then necessary to isolate isobutylene from the mixture which procedure is not only costly, but also inefficient.

The present invention is directed to the conversion of tert-butyl alkanoate to methacrolein and methacrylonitrile by treatment with an appropriate catalyst.

U.S. Pat. No. 4,065,507 discloses a process for preparing methacrolein by the oxidation of tert-butyl alcohol, alkyl tert-butyl ether, isobutylene dimer and/or isobutylene trimer with isobutylene. There is no mention of any tert-butyl esters being oxidized to methacrolein.

Tert-butyl alkanoates are known and their isolation from $C_4$ streams containing isobutylene is also known. See U.S. Pat. No. 3,026,362, Belgian Pat. No. 819,225 and U.S. Pat. No. 4,011,272.

It is an advantage of the present process that the crude isobutylene which is isolated as a tert-butyl alkanoate can now be directly oxidized in the presence of molecular oxygen by passing the tert-butyl alkanoate over a catalyst at elevated temperatures.

This invention comprises a novel process for producing methacrolein or methacrylonitrile by the direct selective oxidation or ammoxidation of a tert-butyl alkanoate, preferably where the alkyl moiety of the alkanoate radical has from 1 to 4 carbon atoms, and includes tert-butyl formate, tert-butyl acetate, tert-butyl propionate, tert-butyl butyrate and the like.

The reaction mixture of tert-butyl alkanoate and molecular oxygen, preferably supplied from air and, optimally, including steam, is passed over a catalyst at an elevated temperature, for example, a temperature in the range of from about 200° to about 600° C.

Any catalyst which can be employed in the oxidation of isobutylene to methacrolein can also be employed in the oxidation or ammoxidation of tert-butyl alkanoate to methacrolein or methacrylonitrile. As examples of the type of catalysts which can be employed there are those disclosed in U.S. Pat. No. 3,907,712 which discloses catalysts of the composition having the following atomic ratios: Co:Fe:Bi:W:Mo:Si:Z is within the range of 2.0–20:0.1–10:0.1–10.0:0.5–10.0:2.0;14 11.5:0.5–15.0:0.005–1.0 wherein Z is an alkali metal; also those disclosed in U.S. Pat. No. 3,936,505 which are catalysts having the formula: $Mo_{12}-X_x-Y_y-O_d$ wherein X represents at least one of Nb and Ta: Y represents at least one of of Te, Bi, Co, W, In and Ti; x is a number from 0.1 to 9; y is a number from 0.2 to 12 and d, which is determined by the oxidation state of each component, is a number from about 36 to about 95 when each component is in the highly oxidized state; also those disclosed U.S. Pat. No. 4,035,418 which are catalysts having the formula;

$Mo_aSb_bBi_cFe_dNi_eCo_fSn_gX_hY_iO_j$ wherein a to j represents the atomic ratio of each component and a is 12, b is 0.2 to 20; c is 0.2 to 12; d is 0.2 to 12; e is 0.2 to 12; f is 0 to 20; g is 0 to 20; h is 0.01 to 4; i is 0.01 to 4; j is a value determined by the valences of the elements in the catalysts, and X is at least one metal selected from the group consisting of potassium, rubidium, cesium, and thalium, and y is at least one metal selected from the group consisting of selenium, tellurium, gallium, vanadium, ruthenium, zinc, niobium, magnesium, chromium, manganese, cadmium, and tantalum; also U.S. Pat. No. 4,111,984, which discloses the catalyst $Mo_aSb_bBi_cFe_d$-$Ni_eSn_fX_gY_hO_i$ wherein X is at least one alkaline metal selected from potassium, rubidium and cesium, Y is at least one metal selected from cobalt, uranium, germanium, tungsten, and titanium, a to h are atomic ratios wherein a=12, b=0.2 to 20, c=0.2 to 12, d=0.2 to 12, e=0.2 to 12, f=0 to 20, g=0.01 to 4, h=0 to 6 and i is the value determined by the state of oxidation of the metal ion components of the catalyst; also U.S. Pat. No. 4,078,004 which discloses not only catalysts but supports for the catalysts.

In general, catalysts employed in this invention are based on oxide combinations selected from Mo-Co, Mo-Bi, Mo-Fe, Mo-P, Mo-Bi-Fe-Co which may also contain Ni, Sb, Te, W, Cs, K, Cu or combinations thereof.

The catalysts compositions described above may be prepared by the methods taught in the above-mentioned patents and also in the following U.S. Pat. Nos. 4,049,577, 3,789,063, British Pat. No. 2,023,597, U.S. Pat. No. 4,001,317.

Neither the catalyst per se nor the preparation of these catalysts form any part of the present invention. These patents are incorporated by reference to the extent necessary to enable those skilled in the art to prepare the catalyst.

In the process of the present invention, a mixture of tert-butyl alkanoate feed in vapor form and molecular oxygen (when methacrolein is desired) or molecular oxygen and ammonia, (when methacrylonitrile is desired), optionally in the presence of steam or other diluents is contacted with a catalyst as described above at an elevated temperature in the range of from about 200° to 600° C., for a contact time sufficient to convert the feed mainly to methacrolein or methacrylonitrile, respectively. The reactor effluent may contain methacrylic acid. The contact time may vary widely, from about 20 seconds or more. The reaction can be conducted under atmospheric, super-atmospheric, or sub-atmospheric pressures. However, in general, pressures near atmospheric, are preferred.

Any source of oxygen may be employed in the process, and, for economic reasons, it is preferred that air be employed as the source of oxygen. The mol ratio of oxygen to the hydrocarbon feed may range from between 0.5:1 to 10:1 with the preferred ratio being in the range of from about 1:1 to about 5:1.

Diluent, such as water, nitrogen, and carbon dioxide, may be present in the reaction mixture.

In general, any apparatus of the type known to be suitable for carrying out oxidation reactions in the vapor phase may be employed in the execution of this process. The process may be conducted either continuously or intermittently. The catalyst bed employed may be either a fixed-bed employing a large particulate or pelleted catalyst or a so-called "fluidized" bed of catalyst.

The reactor may be brought to the reaction temperature before or after the introduction of the reaction feed mixture. However, in a large scale operation, it is preferred to carry out the process in a continuous manner, and in such a system the recycling of any unreacted starting material is contemplated.

The examples disclosed in the specific embodiment are representative of the process conditions and catalyst compositions that are suitable for the process of this invention. However, the scope of the invention is not to be limited by these examples.

EXAMPLE 1

Methacrolein

Step A:

Tert-butyl acetate

To 1800 of a mixed $C_4$ hydrocarbon refinery stream (composition: 36.5% isobutylene, 33% 1-butene, 24% 2-butene, 2.5% n-butene, and 2% isobutane) is added 660 g of glacial acetic acid in an autoclave containing 88 g (dry basis) of a sulfonated styrene-divinylbenzene copolymer marcoreticular resin (200–400 mesh). The reaction is run for 8½ hours at 40° C. at a maximum pressure of 140 lbs. The reaction product is separated from the resin by suction filtration and washed five times with ice water before drying over magnesium sulfate. After filtering to remove the drying agent the crude product is distilled at atmospheric pressure. The fraction distilling between 95°–97° C. is 97% tert-butyl acetate (about 50% yield based on isobutylene charged.)

Step B: Methacrolein

The tert-butyl acetate is fed, along with air and water, to a reactor containing a catalyst of composition: $Mo_{12}P_{3.3}Fe_{0.6}Co_{0.9}Ni_{8.9}Th_{0.05}Sn_{0.05}Sb_{0.31}Te_{0.68}W_{1.2}Ta_{0.6}Cu_{0.9}Zr_{1.2}O_x$ (supported on perlite, 46.3% by weight.)

The reactor is placed in a salt bath at 370° C. and the inlet pressure to reactor is controlled at 20 lbs. The resultant product distribution is given in Table I along with the comparable results for isobutylene fed to the same catalyst under the same conditions. The feeds to the reactor were:

| | |
|---|---|
| Tert-butyl acetate or isobutylene | 72 mmoles/hr. |
| $H_2O$ | 450–500 mmoles/hr. |
| Air | 888 mmoles/hr. |

From Table I (infra) it is seen that the selectivity obtained using tert-butyl acetate is greater than that for isobutylene. Thus, although the $C_4$ conversion using tert-butyl acetate is lower, the amount of methacrolein produced is about the same. The unused isobutylene may be recycled to the mixed $C_4$ stream to increase the isobutylene concentration going into the tert-butyl acetate production. The acetate acid produced in the oxidation, along with the unused portion from the tert-butyl acetate production step can also be recycled back to the tert-butyl acetate production step.

TABLE I

| Compound | Reaction Products (mmoles/hr.) From | |
|---|---|---|
| | Tert-butyl Acetate | Isobutylene |
| Isobutylene | 27.8 | 11.7 |
| Methacrolein (MACR) | 36.6 | 34.4 |
| Methacrylic Acid | 0.5 | 0.4 |
| Acetic Acid | 54.2 | 6.6 |
| Carbon Dioxide | 32.8 | 29.7 |
| Carbon Monoxide | 12.4 | 14.3 |
| Acrylic Acid | 1.5 | 1.8 |
| Acetone | 2.2 | 2.6 |
| $C_4$ conversion | 61.4% | 83.8% |
| MACR selectivity | 87.8% | 65.8% |

EXAMPLE 2

Methacrylonitrile

A gaseous mixture of the tert-butyl acetate, ammonia and air, wherein the mole ratio of ester/ammonia/oxygen is 1/2/2.8, is fed to a reactor containing a bismuth molybdate catalyst. The reactor is immersed in a molten salt bath maintained at 420°–430° C. The gaseous effluent from the reactor is passed through a sulfuric acid scrubber to remove unreacted ammonia. The gaseous effluent from the scrubber is passed into a condensation system to recover the liquid product. The liquid product is analyzed and is found to contain, based on 100 mmoles of tert-butyl acetate, 31 mmoles tert-butyl acetate, 52 mmoles methacrylonitrile, 19 mmoles acetonitrile, 20 mmoles of hydrogen cyanide and 52 mmoles of acetic acid. The conversion of tert-butyl acetate was 69% and the selectivity to methacrylonitrile was 75%.

A similar experiment using isobutylene instead of tert-butyl acetate in the feed resulted in an 83% conversion of isobutylene with a selectivity to methacrylonitrile of 71%.

By following substantially the same procedures as described and by substituting for the tert-butyl acetate other tert-butyl alkanoates and by employing oxygen or ammonia and oxygen the tert-butyl alkanoates can be converted to methacrolein or methacrylonitrile, respectively.

What is claimed is:

1. A process for preparing methacrylonitrile by the vapor phase catalytic ammoxidation of tert-butyl alkanoate wherein the alkyl moiety of the alkanoate radical has from one to four carbon atoms in the presence of oxygen and ammonia at a temperature in the range of from about 200° to 600° C. wherein the catalyst is based on oxide combinations selected from Mo-Co, Mo-Bi, Mo-Fe, Mo-P or Mo-Bi-Fe-Co which may also contain Ni, Sb, Te, W, Cs, K, Cu or combination thereof.

* * * * *